United States Patent [19]
Osborn, III et al.

[11] Patent Number: 5,827,261
[45] Date of Patent: Oct. 27, 1998

[54] MENSTRUAL SHORTS HAVING IMPROVED FASTENING SYSTEM

[76] Inventors: Thomas Ward Osborn, III; Deborah Catherine Schmitz; Nona Jane Redwine, all of 6100 Center Hill Rd., Cincinnati, Ohio 45224

[21] Appl. No.: 878,502

[22] Filed: Jun. 19, 1997

Related U.S. Application Data

[63] Continuation of Ser. No. 594,509, Jan. 31, 1996, abandoned, which is a continuation of Ser. No. 443,105, May 17, 1995, abandoned, which is a continuation of Ser. No. 355,561, Dec. 13, 1994, abandoned, which is a continuation of Ser. No. 96,152, Jul. 22, 1993, abandoned, which is a continuation-in-part of Ser. No. 915,133, Jul. 23, 1992.

[51] Int. Cl.⁶ ................................................. A61F 13/15
[52] U.S. Cl. .................. 604/387; 604/389; 604/390; 604/391; 604/393; 604/396; 604/397; 604/398
[58] Field of Search ................ 604/385.1, 386–394, 604/396–398, 402

[56] References Cited

U.S. PATENT DOCUMENTS

| | | | |
|---|---|---|---|
| 2,016,355 | 10/1935 | Alsop | 604/396 |
| 2,043,325 | 6/1936 | Jackson, Jr. | 604/397 X |
| 2,052,598 | 9/1936 | Berg . | |
| 2,596,127 | 5/1952 | Carmean | 604/396 |
| 2,636,494 | 4/1953 | Hon | 604/396 |
| 3,088,462 | 5/1963 | Mato | 604/394 X |
| 3,489,149 | 1/1970 | Larson . | |
| 3,608,551 | 9/1971 | Seijo | 604/396 |
| 4,340,058 | 7/1982 | Pierce et al. | 604/385.1 |
| 4,560,381 | 12/1985 | Southwell . | |
| 4,605,405 | 8/1986 | Lassen | 604/386 X |
| 4,609,373 | 9/1986 | Johnson | 604/385.1 X |
| 4,666,440 | 5/1987 | Malfitano | 604/385.1 X |
| 4,753,648 | 6/1988 | Jackson | 604/389 |
| 4,804,380 | 2/1989 | Lassen et al. | 604/393 X |
| 4,813,950 | 3/1989 | Branch . | |
| 4,940,463 | 7/1990 | Leathers et al. . | |
| 5,007,906 | 4/1991 | Osborn, III et al. | 604/386 X |
| 5,171,302 | 12/1992 | Buell . | |
| 5,176,668 | 1/1993 | Bernardin . | |
| 5,176,669 | 1/1993 | Klemp . | |
| 5,176,672 | 1/1993 | Bruemmer et al. . | |
| 5,197,959 | 3/1993 | Buell . | |
| 5,197,960 | 3/1993 | Nomura et al. . | |

FOREIGN PATENT DOCUMENTS

| | | | |
|---|---|---|---|
| 5103812 | 4/1993 | Japan | 604/389 |
| 1329868 | 9/1973 | United Kingdom . | |
| WO9301785 | 2/1993 | WIPO . | |
| WO 94/02098 | 2/1994 | WIPO . | |

*Primary Examiner*—Mary Beth Jones
*Attorney, Agent, or Firm*—Theodore P. Cummings; Jeffrey V. Bamber; Steven W. Miller

[57] ABSTRACT

The female protection system of the present invention includes a menstrual short having an outer protective layer and an inner gusset layer. A catamenial pad assembly is connectable to the menstrual short and includes front and rear ends. The catamenial pad assembly includes an absorbent member for absorbing menses and a cinch for biasing the absorbent member into the gluteal groove and against the perineum of the female when worn. A first fastener is provided on the front end of the catamenial pad assembly for attaching the catamenial pad assembly to a first mating surface that is provided at a front attachment location on at least one of the inner gusset layer and the outer protective layer. A second fastener is provided on the rear end of the catamenial pad assembly for attaching the catamenial pad assembly to a second mating surface that is provided at a rear attachment location on at least one of the inner gusset layer and the outer protective layer. The front and rear attachment locations are positioned to cause the cinch to bias the absorbent member of the catamenial pad assembly into the gluteal groove and against the perineum of the female when worn.

13 Claims, 4 Drawing Sheets

MENSTRUAL SHORTS HAVING IMPROVED FASTENING SYSTEM

This application is a continuation of application Ser. No. 08/594,509, filed Jan. 21, 1996, now abandoned, which is a continuation of application Ser. No. 08/443,105 filed May 17, 1995, now abandoned, which is a continuation of application Ser. No. 08/355,561 filed Dec. 13, 1994, now abandoned, which is a continuation of application Ser. No. 08/096,152 filed Jul. 22, 1993, now abandoned, which is a continuation-in-part of application Ser. No. 07/915,133 filed Jul. 23, 1992.

BACKGROUND OF THE INVENTION

1. Technical Field

This invention relates generally to feminine menstrual protection devices and, more particularly, to a catamenial pad assembly that is attachable to menstrual shorts for inhibiting the leakage of menses.

2. Background Art

As is known, disposable catamenial pads are commercially available in a wide variety of configurations for the specific purpose of absorbing and retaining menstrual fluids and other vaginal discharges. Unfortunately, a primary failure mechanism associated with catamenial pads is the leakage of menses from a rear portion thereof due to poor fit in the gluteal groove and against the perineum of the female wearer. Such leakage is most prevalent during night time use of catamenial pads and typically results in soiling of the female wearer's undergarments, clothing and bedding.

To provide additional protection against leakage, it is known to use a washable and reusable garment, such as a menstrual short or panty, in combination with a disposable catamenial pad. For example, U.S. Pat. No. 3,489,149 to Larson discloses a washable menstrual panty having a small pocket in the crotch area for retaining a disposable catamenial pad. Since the menses must initially flow through a layer of material forming the pocket to reach the catamenial pad, removal of the soiled catamenial pad can be distasteful, difficult and unsanitary. While a new pad can be inserted into the pocket, the garment is already soiled and would typically be changed. Also, the pocket may not accommodate the varied sizes of catamenial pads currently on the market. Finally, the menstrual panty is not adapted to deliberately position the catamenial pad for preventing leakage of menses from the rear portion thereof.

Various other menstrual shorts or panties are known which also fail to adequately address the need for properly positioning and retaining the disposable catamenial pad in the pudendal region of the female wearer. For example, U.S. Pat. No. 4,560,381 to Southwell describes a mesh-like outer panty shell with a thick inner layer of absorbent material in the lower crotch area of the panty. The inner layer of absorbent material includes a depression for receiving and positioning a catamenial pad. In U.S. Pat. No. 4,813,950 to Branch, a washable menstrual panty is disclosed as having an outer lining of spandex, soft tricot, etc. and an inner lining of soft plastic film to prevent passage of menses therethrough. Alternatively, existing Japanese-style menstrual shorts act like a girdle or very tight fitting panty which holds the catamenial pad in the wearer's pudendal region. However, positioning of the catamenial pad is achieved by the tightness of the menstrual short which, in turn, may cause discomfort to the wearer.

In each of the above-noted menstrual shorts, the catamenial pad is not positioned and retained by the menstrual shorts in the gluteal groove and against the perineum to prevent leakage of menses from the rear portion of the catamenial pad. Rather, such known menstrual garments are typically designed to position the catamenial pad near the vaginal vestibule and attempt to prevent leakage of menses by using liquid impervious layers or boundaries.

It is therefore an object of the present invention to provide an improved feminine menstrual protection system for locating and retaining a disposable catamenial pad in the gluteal groove and against the perineum of the female wearer's body. Labial contact may also be provided.

It is a related object of the present invention to provide a menstrual short or panty that is adapted to retain a removable catamenial pad assembly for enhanced pudendal/pad contact and reduced leakage of menses from the rear of the disposable catamenial pad, and yet which may be looser fitting and more comfortable than conventional menstrual garments.

As a further object of the present invention, the removable catamenial pad assembly includes a disposable catamenial pad and a lifting mechanism for supporting and biasing the catamenial pad into enhanced body contact.

These and various other objectives of the present invention will be more readily apparent when considered in reference to the following description and when taken in conjunction with the accompanying drawings.

SUMMARY OF THE INVENTION

The present invention is directed to a female menstrual protection system comprised of a menstrual garment and a catamenial pad assembly that is connectable to the menstrual garment. The menstrual garment of the present invention is a washable and reusable panty or short having an outer layer defining first and second leg openings for receiving the legs of a female wearer. In addition, an inner layer or gusset-type liner is provided between the first and second leg openings and is attached to the outer layer. The catamenial pad assembly includes an absorbent pad for absorbing and retaining menstrual fluids and a lifting mechanism for lifting the absorbent pad into the gluteal groove and against the perineum of the wearer.

In one preferred form, the lifting mechanism is an elongated cinch that is adapted to support and lift the absorbent pad into the gluteal groove and against the perineum of the female, thereby providing sustained body contact for inhibiting leakage of menses from a rear portion of the absorbent pad. In addition, the lifting mechanism includes a fastener system for removably attaching the elongated cinch to the menstrual garment. The fastener system includes a first fastener provided on a front end portion of the catamenial pad assembly for attaching the catamenial pad assembly to a first mating surface provided at a front attachment location on at least one of the inner gusset layer and the outer protective layer. The first mating surface cooperates with the first fastener to attach the front end of the catamenial pad assembly to the menstrual short. In addition, a second fastener is provided on a rear end portion of the catamenial pad assembly for attaching the catamenial pad assembly to a second mating surface provided at a rear attachment location on at least one of the inner gusset layer and the outer protective layer. The second mating surface cooperates with the second fastener to attach the rear end of the catamenial pad assembly to the menstrual short. The front and rear attachment locations are positioned for causing the elongated cinch to bias the absorbent pad into the gluteal groove and against the perineum of the female wearer. It is a feature of the present invention that the front attachment location be positioned at least anterior to the anus of the female and, more preferably, be located adjacent the vaginal vestibule of the female wearer. Likewise, the rear attachment location is preferably positioned at least 2.75" from a lowest portion of the outer protective layer when the menstrual short is folded flat along first and second lateral sides thereof.

BRIEF DESCRIPTION OF THE DRAWINGS

While the specification concludes with claims particularly pointing out and distinctly claiming the subject matter which is regarded as forming the present invention, it is believed that the present invention will be better understood from the following description when taken in conjunction with the accompanying drawings in which:

DESCRIPTION OF THE PREFERRED EMBODIMENT

The present invention relates generally to washable and reusable menstrual garments and, more particularly, to a menstrual short or panty adapted to retain and support a lifting mechanism that is provided for lifting a catamenial pad into enhanced contact with the female wearer's pudendal region. As an additional feature, the lifting mechanism is adapted to cause the catamenial pad to be lifted into intimate contact with the gluteal groove and against the perineum of the female wearer for inhibiting leakage of menses for the rear portion of the catamenial pad.

As used herein, the term "catamenial pad" refers to an absorbent article which is worn by females adjacent to the pudendal region for absorbing and containing menstrual fluids and other vaginal discharges, and "disposable" refers to an absorbent article which is intended to be discarded after a single use. As used herein, the term "pudendal" refers to the externally visible female genitalia and is limited to the labia majora, the labia minora, the clitoris and the vaginal vestibule. In addition, the term "perineum" refers to the external region of the female's body between the anus and the pudendal region while the term "gluteal groove" refers to the crevice between the buttocks extending upwardly from the perineum.

Figure 1:
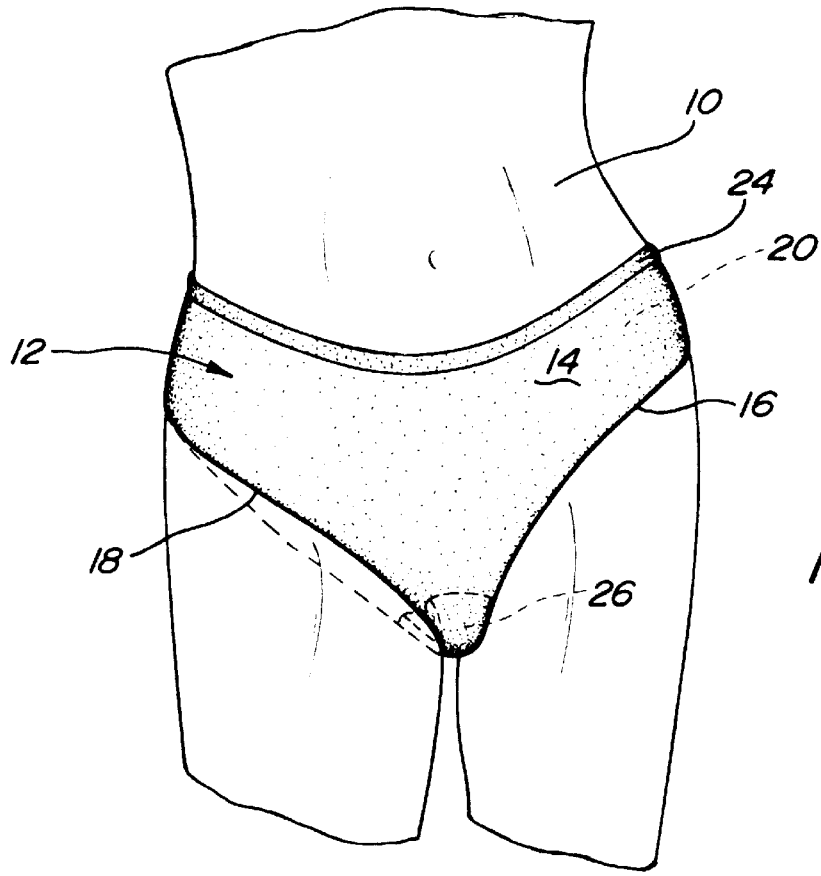
FIG. 1 is a front view of a menstrual short according to the prior art and which is shown being worn by a female.
Figure 2:
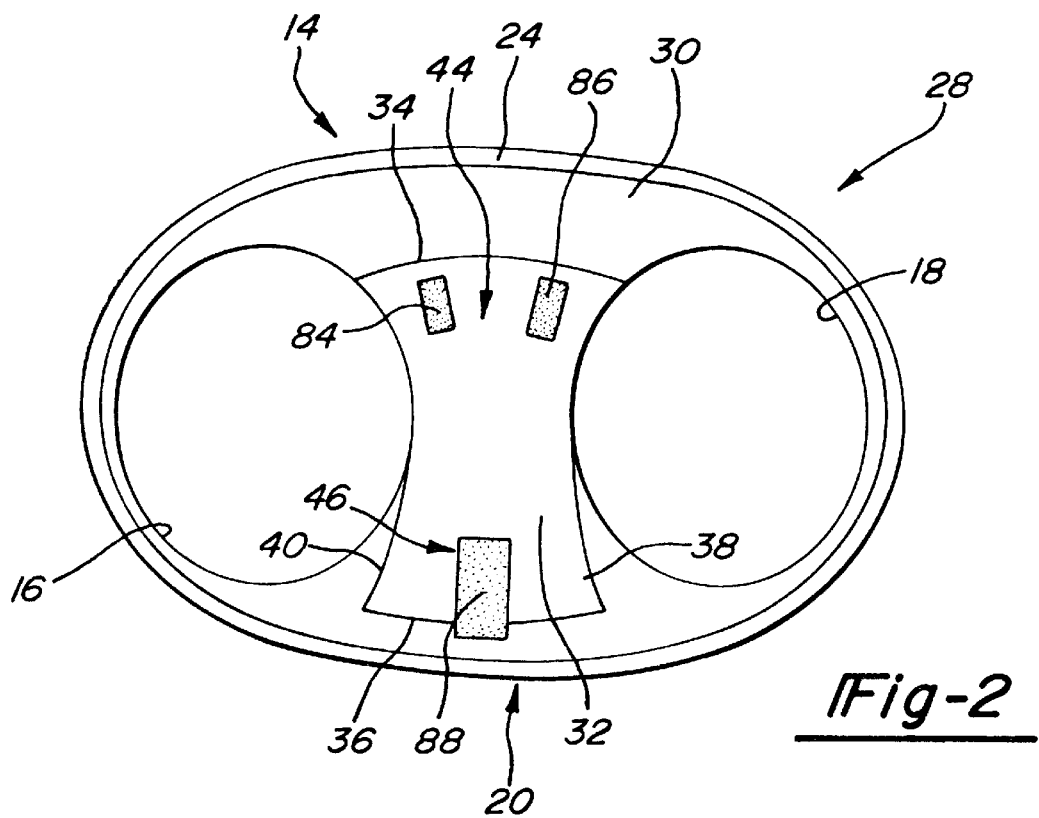
FIG. 2 is a plan view of an improved menstrual panty according to the present invention.

In FIG. 1, a female 10 is shown wearing a prior art menstrual short or panty 12 having a front portion 14, first and second leg openings 16 and 18, a rear portion 20, and an elastic waistband 24 for maintaining the menstrual short 12 on the female 10. Elastic or other resilient material may be provided around the first and second leg openings 16 and 18 to further provide a conforming fit. The menstrual panty 12 can be any style, for example "bikini", "tanga", "French cut", American style, or Japanese menstrual shorts. In addition, a disposable catamenial pad 26 is shown positioned by the menstrual short 12 adjacent the perineum and pudendal regions of the female 10 in a conventional manner.

Referring now to FIGS. 2 through 6, a menstrual short or panty 28 incorporating the novel features of the present invention is shown. For purposes of clarity, like reference numerals are used where appropriate. In general, menstrual short 28 is an improvement over prior art menstrual short 12 in view of its use in cooperation with a lifting mechanism 29 that is adapted to lift an absorbent catamenial pad into enhanced contact with the female's pudendal and perineum regions to provide sustained placement relative thereto under all motion and use conditions. As a result, the likelihood of leakage of menses from the rear of the catamenial pad (i.e., along the perineum or the gluteal groove) is significantly reduced.

The menstrual short 28 includes an outer layer 30 defining the "shell" of the panty worn by the female wearer and an inner protective layer or gusset-type liner 32. As seen, outer layer 30 includes the front portion 14, the rear portion 20, the leg openings 16 and 18, and the elastic waistband 24. The gusset-type liner 32 is attached to the outer layer 30 in the crotch area of the menstrual short 28 and extends from a region anterior to the vaginal vestibule of the female 10 toward the elastic waistband 24 in the rear portion 20 of outer layer 30. More particularly, the gusset 32 has a generally hour-glass shape and includes a front edge 34, a rear edge 36, and a pair of lateral edges 38 and 40. The front edge 34, the rear edge 36, and the lateral edges 38 and 40 of the gusset-type liner 32 are attached to the outer layer 30, as by sewing, gluing, or any other suitable means. Moreover, the rear edge 36 of the gusset-type liner 32 need not extend completely to the elastic waistband 24 in the rear 20 of the menstrual short 28. In addition, it is contemplated that front and rear attachment locations, generally indicated by arrows 44 and 46, respectively, can be located on the outer layer 30 or on the inner protective layer 32, or both. Preferred positions for the front and rear attachment locations 44 and 46, respectively, will be described in greater detail below.

Figure 3:
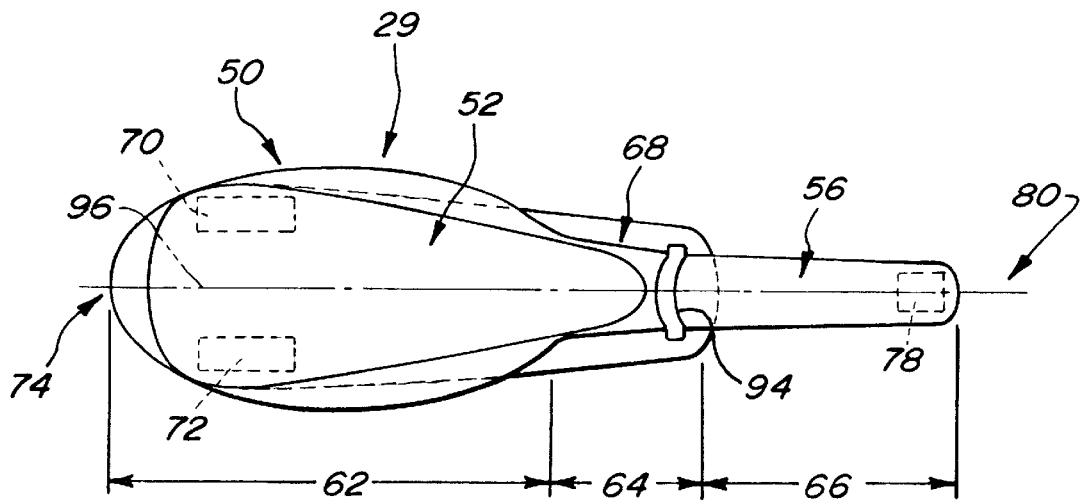
FIG. 3 is a plan view of a catamenial pad assembly according to the present invention.
Figure 4:
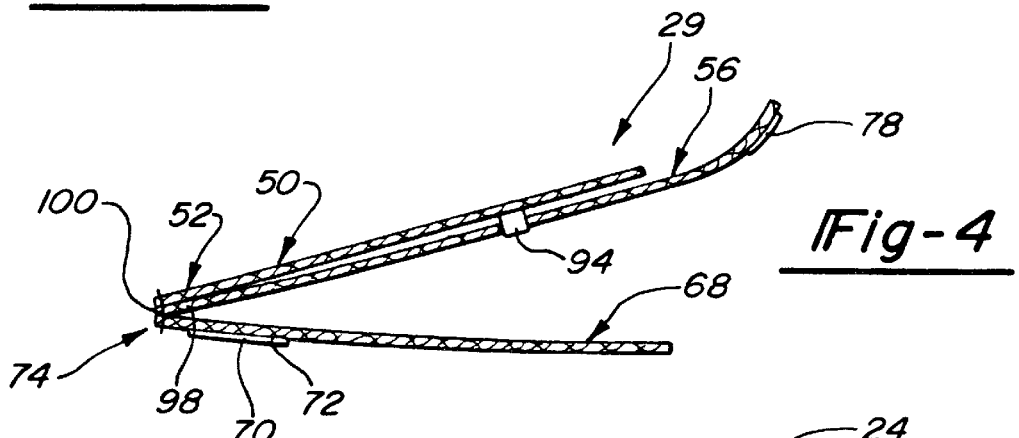
FIG. 4 is a side view of the catamenial pad assembly shown in FIG. 3.
Figure 5:
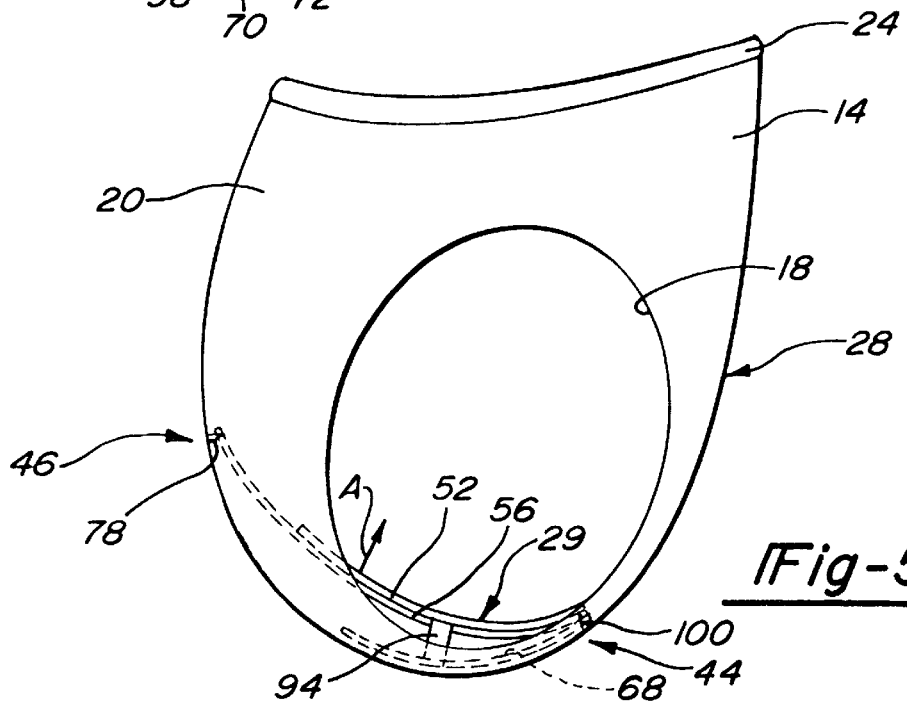
FIG. 5 is a side view of the catamenial pad assembly of FIGS. 3 and 4 fastened to the menstrual panty of FIG. 2.

From FIG. 3 through 6, lifting mechanism 29 is shown as a catamenial pad assembly 50 that is removably secured to menstrual panty 28 for lifting an absorbent catamenial pad 52 toward the female wearer's perineum and gluteal groove while providing some degree of inter labial contact. As a result, leakage of menses from a rear portion of the absorbent catamenial pad 52 is avoided, thereby inhibiting the undesirable soiling of the menstrual short 28 and other surrounding clothing and/or bedding. In general, this "lifting" action is obtained by using the differential stretch attributes of the various components associated with catamenial pad assembly 50 and its specific attachment locations. In one preferred form, the lifting mechanism 29 includes an elongated cinch 56 that is shown in FIG. 5 lifting the catamenial pad 52 in an upward direction, as indicated by arrow "A". The cinch 56 is an elongate strip of an elastic material having an elasticity ranging from taut to flaccid depending upon the particular fit desired. Alternatively, the cinch 56 can be made of a material having a low modulus of elasticity similar to panty fabric. Regardless of the specific material chosen, the cinch 56 should only provide sufficient upward lift to promote enhanced and sustained pad contact while preventing discomfort to the female 10 when worn.

The cinch 56 is located beneath catamenial pad 52 and improves contact between the catamenial pad 52 and the pudendal region of the female 10 when worn. The cinch 56 is shown to be spoon-shaped and includes a forward section 62, a central section 64, and a rear section 66. The forward section 62 is shown to be oval-shaped while the central and rear sections 64 and 66 are generally elongated strips. However, other shapes and materials for the cinch 56 will be readily apparent. In one preferred form, the forward and rear sections 62 and 66 can be made of a relatively inelastic material with the central section 64 made of an elastic material.

With particular reference to FIGS. 2 through 5, catamenial pad assembly 50 is also shown to include a backing sheet 68 located beneath the cinch 56 and which includes front fasteners 70 and 72 that are generally located adjacent a front end 74 of the catamenial pad assembly 50. In addition, a rear fastener 78 is generally located at a rear end 80 of the elongated cinch 56. While two front fasteners 70 and 72 are shown, one front fastener or more than two front fasteners can be used. Similarly, while only one rear fastener 78 is shown, two or more rear fasteners can be used.

The front fasteners 70 and 72 on the backing sheet 68 are aligned to attach at the front attachment location 44 to front mating surfaces 84 and 86. It is contemplated that front mating surfaces 84 and 86 be located on either, or both, of the outer layer 30 and gusset-type liner 32. Similarly, the rear fastener 78 on the cinch 56 is aligned to attach at the rear attachment location 46 to a rear mating surface 88 which again can be located on either, or both, of the outer layer 30 and gusset-type liner 32. As will also be appreciated, the front mating surfaces 84 and 86 and the rear mating surface 88 can be of variable length to allow quick and simple user adjustment. Such adjustment of the attached position of the catamenial pad assembly 50 results in a corresponding adjustment in the amount of upward lift applied by the cinch 56 on catamenial pad 52.

As an additional feature, a loop or guide 94 can be provided for positioning the cinch 56 along a center portion 96 of the catamenial pad assembly 50. Opposite ends of the loop or guide 94 can be attached to the backing sheet 68 as shown in FIGS. 3 and 5 or, in the alternative, to the absorbent catamenial pad 52 as shown in FIG. 4.

The particular embodiment shown in FIGS. 3 through 5 illustrates a catamenial pad assembly 50 that is disposable and intended for a single use. To this end, the cinch 56 and the backing sheet 68 are attached to the absorbent catamenial pad 52 to form a flexible hinge 100 at the front end 74 of the catamenial pad assembly 50. Other methods of attaching the absorbent catamenial pad 52, the cinch 56, and the backing sheet 68 together as an assembly will be readily apparent. The catamenial pad assembly 50 may also be used without the backing sheet 68. In such case, the front fasteners 70 and 72 would be located on a front end portion of the cinch 56 or, alternatively, on a leading end of the absorbent catamenial pad 52.

To provide means for releasably securing catamenial pad assembly 50 to menstrual panty 28, the front and rear fasteners 70, 72, and 78 could be adhesive patches while the front and rear mating surfaces 84, 86 and 88 could be release-coated bonding surfaces, such as silicone-coated patches of polyolefinic material. Alternately, the front and rear mating surfaces 84, 86, and 88 could be adhesive patches while the front and rear fasteners 70, 72 and 78 could be release coated bonding surfaces. In addition, other types of fasteners and mating systems are contemplated. For example, the front and rear fasteners 70, 72, and 78 could be hook-type members and the front and rear mating surfaces 84, 86, 88 could be made of a looped material. Moreover, the front and rear mating surfaces 84, 86 and 88 can be formed integrally with the menstrual short 28 or can be added to a conventional menstrual short, such as the menstrual short 12 of FIG. 1.

To achieve the requisite upward lift, the front attachment location 44 for the cinch 56 should be located at least anterior to an anus of the female 10 when worn, as depicted by arrow "A" in FIG. 5. More preferably, the front attachment location 44 for the cinch 56 should be located adjacent the vaginal vestibule of the female 10 when worn. However, other front attachment locations 44 are readily apparent. Similarly, the rear attachment location 46 for the cinch 56 should be located sufficiently high in the rear portion 20 of the menstrual shorts 28 to provide the upward lift required to bias the absorbent pad 52 of the catamenial pad assembly 50 into the gluteal groove and against the perineum of the female 10. Positioning the rear attachment location 46 above a curvature of the buttocks of the female wearer 10 when worn is typically sufficient to provide the desired vertical lift. However, positioning the rear attachment location 46 in close proximity to the waistband 24 is also desirable. Alternatively, the rear attachment location 46 can be located on an outer surface of the menstrual short 28 requiring the rear end 80 of the cinch 56 to be pulled out and over the waistband. Again, other rear attachment locations 46 will be readily apparent to those skilled in the art. However, it will be appreciated that the specific position of the rear attachment location 46 relative to the waistband 24 will vary depending on the style of the menstrual short 28 and comfort of the female 10 when the menstrual short 28 is worn. Furthermore, the shape of the buttocks of the female 10, which varies according to ethnic background, also effects the positioning of the rear attachment location 46 relative to the waistband 24.

Figure 6:
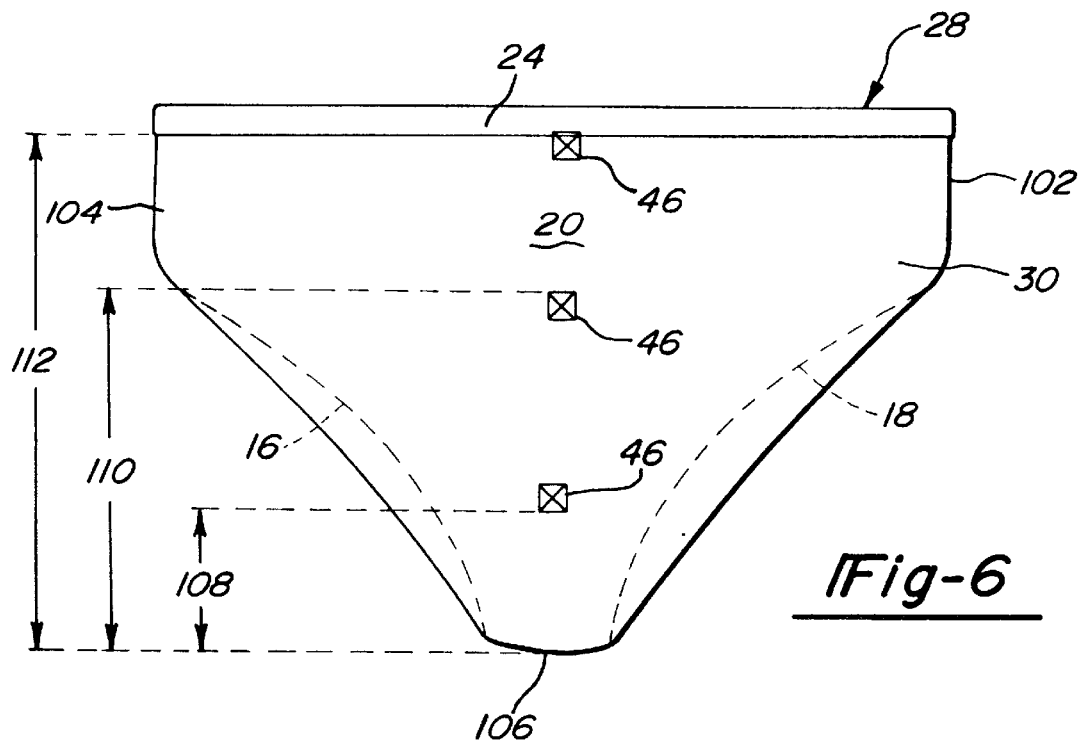
FIG. 6 is a rear view of the menstrual panty of FIG. 2 folded along lateral sides thereof.

With particular reference to FIG. 6, the menstrual short 28 is shown folded flat along first and second sides 102 and 104 thereof with various rear attachment locations 46 for the cinch 56 shown in greater detail. At a minimum, the rear attachment location 46 for the cinch 56 is preferably located at least 2.75" from a lowest portion 106 of the outer layer 30 when the menstrual short 28 is folded along the first and second lateral sides 102 and 104, as shown at 108. However, the rear attachment location 46 is more preferably located at least six or seven inches from the lowest portion 106, as respectively shown at 110 and 112, when the menstrual short 28 is folded. As noted, the rear attachment location 46 can also be located on the outer surface of the outer protective layer 30 if desired. As also noted, the rear attachment location 46 and the rear mating surface 88 can be elongate to allow user adjustment of the amount of lift generated by cinch 56.

Figure 7:
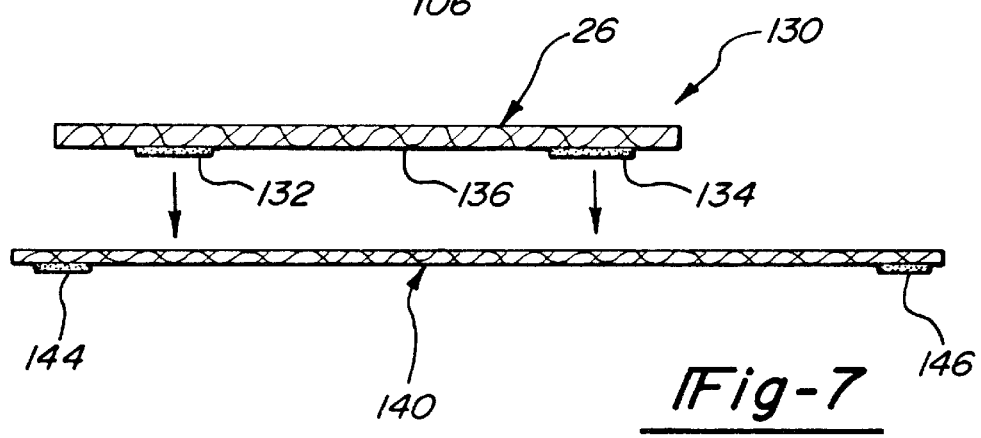
FIG. 7 is a side view of an alternate embodiment of the catamenial pad assembly of the present invention showing a conventional disposable catamenial pad used in cooperation with an elongated cinch member.
Figure 8:
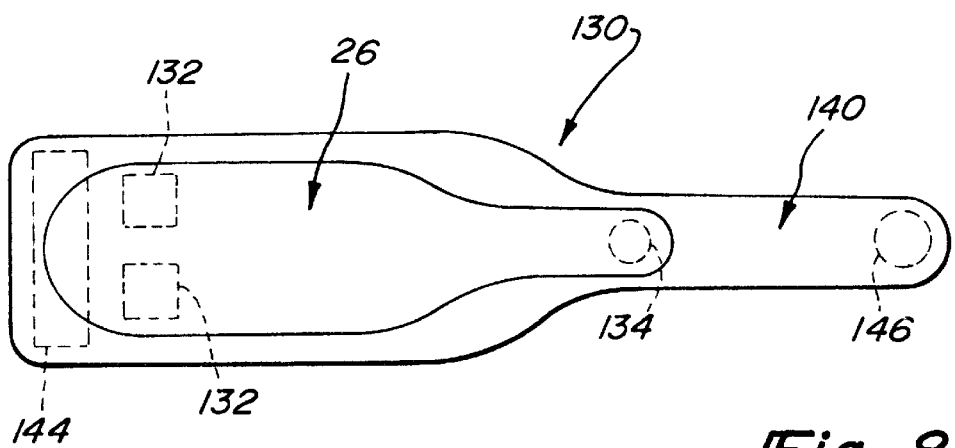
FIG. 8 is a plan view of the alternate embodiment of FIG. 7 showing the conventional disposable catamenial pad fastened to the cinch.
Figure 9:
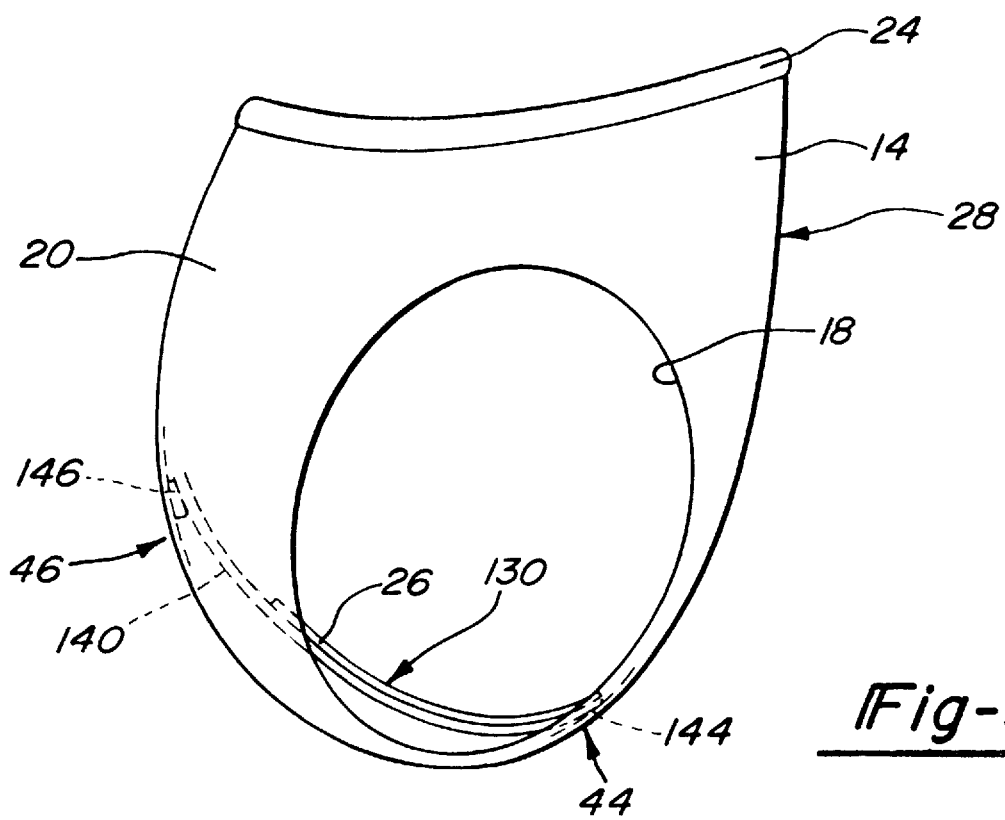
FIG. 9 is a side view of the conventional catamenial pad and cinch arrangement of FIGS. 7 and 8 fastened to the menstrual panty of FIG. 2.

Referring now to FIGS. 7 through 9, an alternate embodiment incorporating further features of the present invention is shown. More particularly, a modified version of a reusable catamenial pad assembly 130 is disclosed which is adapted to retain a disposable catamenial pad 26 thereon. More specifically, conventional catamenial pad 26 includes front adhesive fasteners 132 and rear adhesive fasteners 134 on a liquid impervious backing sheet 136 thereof and which are normally used to attach the disposable catamenial pad 26 inside conventional shorts or panties, for example the menstrual shorts 12 of FIG. 1. The catamenial pad 26 can be made of a variety of different materials and have a variety of different shapes, lengths and thicknesses. In the particular embodiment shown, the catamenial pad 26 is attached to a cinch 140 which includes front and rear fasteners 144 and 146, respectively, for fastening the cinch 140 at the front and the rear attachment locations 44 and 46, respectively, shown in FIG. 2. More particularly, the front fastener 144 can mate with both of the front mating surfaces 84 and 86 or alternatively only one or multiple front mating surface(s) may be provided. The cinch 140 can be covered with or made of a material impervious to menses, (e.g., a non-staining material).

Preferably, each of the above-described catamenial pad assemblies is used in combination with thin, flexible catamenial pads to allow the cinch to better conform the thin, flexible catamenial pad to the pudendal region. Thus, the cinch is preferably made of soft, flexible and absorbent material. One suitable material for the cinch is nylon panty fabric. More preferably, the cinch is extensible. As seen, the force required to stretch the cinch is preferably less than the force required to stretch the menstrual shorts 28 the same distance to allow the cinch to remain in position when the menstrual shorts 28 move or stretch. The front and rear mating surfaces can be elongated or can include multiple front and rear mating surfaces (for example when hook and loop fasteners are used) to allow the female 10 to select a point of attachment.

As can be appreciated from the foregoing, menstrual shorts incorporating the present invention reduce soiling by providing enhanced body contact and sustained positioning of the catamenial pad under various body motions and user conditions. Additionally, the menstrual short or panty may have a looser fit than prior menstrual shorts while providing greater leakage prevention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A feminine protection system for preventing leakage of menses when said system is worn by a female wearer comprising:

a menstrual short comprising an outer protective layer and an inner gusset layer;

an adjustable catamenial pad assembly connectable to the menstrual short, said catamenial pad assembly comprising front and rear ends, a lifting mechanism an absorbent means attached to said lifting for mechanism absorbing menses, said lifting mechanism comprising a backing sheet positioned below a cinch, the cinch having variable elasticity along its length, said backing sheet and said cinch being attached together at said front end of said catamenial pad assembly to thereby form a flexible hinge;

first fastening means for removably attaching said front end of said catamenial pad assembly to a front attachment location provided on at least one of said inner gusset layer and said outer protective layer, said front attachment location being attached to be located at least anterior to the anus of a female wearer; and second fastening means for removably attaching said rear end of said catamenial pad assembly to a rear attachment location provided on at least one of said inner gusset layer and said outer protective layer, said rear attachment location being located at a position sufficiently high in the rear portion of the menstrual short to provide upward lift to said catamenial pad assembly;

wherein said front attachment location is adapted to be positioned adjacent the vaginal vestibule and below said rear attachment location such that the positioning of said front attachment location and said rear attachment location of said lifting mechanism provides upward lift to bias said absorbent means of said catamenial pad assembly into the gluteal groove and against the perineum of the female wearing said menstrual short.

2. The feminine protection system of claim 1 wherein said front attachment location is provided on said inner gusset layer and said rear attachment location is provided on said outer protective layer.

3. The feminine protection system of claim 1 wherein said absorbent means is angularly positioned into the gluteal groove by said lifting mechanism.

4. The feminine protection system of claim 1 wherein said rear attachment location is positioned at least 2.75" from a lowest portion of said outer protective layer when said menstrual short is folded flat along first and second lateral sides thereof.

5. The feminine protection system of claim 1 wherein said rear attachment location is positioned adjacent a rear waistband portion of said menstrual short.

6. The feminine protection system of claim 1 wherein said first and second fastening means are adhesive patches.

7. The feminine protection system of claim 1 wherein said second fastening means is provided on said rear end of said lifting mechanism for attachment to said rear attachment location.

8. The feminine protection system of claim 1 wherein said cinch further comprises elastic and inelastic portions.

9. The feminine protection system of claim 8 wherein said front and rear end regions of said cinch comprise inelastic portions.

10. The feminine protection system of claim 1 wherein said absorbent means is thin and flexible.

11. An adjustable catamenial pad assembly having front and rear ends, said catamenial pad assembly comprising:

a lifting mechanism comprising a backing sheet attached to a wearer's undergarment and a cinch having varying elasticity along its length, said cinch being positioned above said backing sheet and attached to said backing sheet at said front end of said catamenial pad assembly to thereby form a flexible hinge; and a thin, flexible absorbent means positioned onto said cinch facing upwards towards a wearer's pudendal and gluteal regions, said flexible hinge of said lifting mechanism providing a bias to fit said absorbent means into the gluteal groove and against the perineum of a female wearing said adjustable catamenial pad assembly.

12. The feminine protection system of claim 11 wherein said cinch further comprises elastic and inelastic portions.

13. The feminine protection system of claim 12 wherein said front and rear end regions of said cinch comprise inelastic portions.

* * * * *